(12) United States Patent
Luo

(10) Patent No.: US 11,872,346 B1
(45) Date of Patent: Jan. 16, 2024

(54) BREATHING MASK WITH A FOAM PAD

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/324,255

(22) Filed: May 26, 2023

(51) Int. Cl.
*A61M 16/06* (2006.01)

(52) U.S. Cl.
CPC ..... *A61M 16/0622* (2014.02); *A61M 2207/10* (2013.01)

(58) Field of Classification Search
CPC .......... A61M 16/0066; A61M 16/0069; A61M 16/06; A61M 16/0611; A61M 16/0616; A61M 16/0622; A61M 16/0633; A61M 16/0666; A61M 16/0683; A61M 16/0694; A61M 16/0816; A61M 16/0825; A61M 16/0841; A61M 16/0875; A61M 16/1055; A61M 16/107; A61M 16/109; A61M 16/1095; A61M 16/16; A61M 2202/0085; A61M 2202/0225; A61M 2205/3344; A61M 2205/42; A61M 2205/59; A61M 2207/00; A61M 2210/0618; A61M 2210/0625

See application file for complete search history.

(56) References Cited

U.S. PATENT DOCUMENTS

| | | | | | |
|---|---|---|---|---|---|
| 10,799,661 | B2* | 10/2020 | Eves | ................. | A61M 16/0825 |
| 10,926,050 | B2* | 2/2021 | Eves | ................. | A61M 16/0066 |
| 11,213,702 | B1* | 1/2022 | Scheiner | ............ | A41D 13/1161 |
| 2003/0145859 | A1* | 8/2003 | Bohn | ................. | A61M 16/0616 |
| | | | | | 128/206.28 |
| 2010/0294281 | A1* | 11/2010 | Ho | .................... | A61M 16/0633 |
| | | | | | 128/206.24 |
| 2022/0111171 | A1* | 4/2022 | Eves | ................. | A61M 16/0683 |

* cited by examiner

*Primary Examiner* — Annette Dixon
(74) *Attorney, Agent, or Firm* — Hamre, Schumann, Mueller & Larson, P.C.

(57) ABSTRACT

A breathing mask includes a rigid member, an elastic member, and a foam member. The rigid member has an interface on the side away from the user's face for accessing the breathing gas of the continuous positive airway pressure device, and a flared joint on the side adjacent to the user's face. The elastic member is in communication with the inner cavity of the rigid member and is fixedly connected to the flared joint. The side of the elastic piece adjacent to the user's face at least partially abuts the user's nasal bridge area to form an elastic body part, and a support part connected to the elastic body part is provided on the side of the elastic member adjacent to the user's face. The foam member is fixed to the support part and, together with the elastic member, forms a sealing surface for fitting the user's face.

20 Claims, 14 Drawing Sheets

BREATHING MASK WITH A FOAM PAD

TECHNICAL FIELD

The present disclosure relates to the technical field of breathing masks, particularly to a breathing mask with a foam pad, which is suitable for accommodating a portion of the user's face to prevent leakage of pressurized gas supplied to the user.

BACKGROUND

Obstructive sleep apnea is a sleep-related breathing disorder caused by relaxation of the muscles in the tongue, soft palate, and oropharyngeal posterior wall area during sleep, usually leading to the patient stopping breathing for 10 seconds or more at a time, with this condition occurring 5-30 times or more per hour. The persistence of this condition leads to excessive daytime sleepiness, snoring at night, morning headaches, and potential complications such as cardiovascular disease and brain injury in patients. Currently, continuous positive airway pressure ventilation therapy is mainly used to treat obstructive sleep apnea, involving a CPAP (Continuous Positive Airway Pressure) machine, an airway for delivering air, and a mask system that seals the user's nose and/or mouth. Due to the complex three-dimensional shape of the face and the different skeletal contours of each individual, the design of the mask system presents many challenges, one of which is that the mask must be able to effectively seal the user's face.

Common masks on the market adhere to the facial contours through a smooth sealing surface, which is usually made of an elastomer, such as rubber or silicone. Due to the different facial contours of different users, the sealing surface cannot fully fit the faces of all users, and to ensure a seal, the user can only apply pressure to the mask by tightening the head strap to achieve a sealing effect. Since the mask's sealing surface is designed to accommodate the user's facial structure, it is not flat, and tightening the head strap applies different pressures to different areas of the face. When the mask achieves a sufficient sealing effect, the pressure produced on the face by long-term wearing becomes unbearable for the user, and due to the non-breathable material of the sealing surface, wearing an overly tight mask for an extended period may cause skin irritation or redness. Additionally, if the user's face has oil or sweat during sleep, it will reduce the sealing performance of the mask.

To alleviate the discomfort caused by the aforementioned masks, users often pad the mask's sealing surface with mask liners, which can reduce pressure sores caused by close contact with the skin. However, during sleep, the head, facial bones, and muscles all have a certain degree of movement, which may cause the liner to shift or fall off during treatment, leading to poor sealing.

SUMMARY

Based on this, it is necessary to address the above-mentioned shortcomings and provide a breathing mask with a foam pad that can fit the faces of most users and has a good sealing effect.

A breathing mask is configured to surround the user's nose and mouth and form a sealing area between the lower lip area and the nasal bridge area or surround the user's nose and form a sealing area between the upper lip area and the nasal bridge area, and supply pressurized breathing gas to the user's airway, including:

A rigid member with an interface on the side far away from the user's face for accessing the breathing gas of the continuous positive airway pressure device, and with a flared joint on the side adjacent to the user's face, when worn by the user;

An elastic member that is in communication with the inner cavity of the rigid member and is fixedly connected to the flared joint, the side of the elastic member adjacent to the user's face at least partially abutting the user's nasal bridge area to form an elastic body part, and a support part connected to the elastic body part being provided on the side of the elastic member adjacent to the user's face; and A foam member, which is fixed to the support part and forms, together with the elastic member, a sealing surface for fitting the user's face;

The inner edge of the foam member is flush with the inner edge of the support part, or the inner edge of the foam member protrudes from the inner edge of the support part.

In one embodiment, the elastic body part corresponds to the user's nasal bridge area or/and cheek area, and the lower area of the elastic body part is concave and forms the support part corresponding to the user's mouth area.

In one embodiment, the elastic body part corresponds to the user's mouth area, and the inner upper area of the elastic body part is concave and forms the support part corresponding to the user's nasal bridge area or/and cheek area.

In one embodiment, the elastic body part corresponds to the user's nasal bridge area and mouth area, and the inner middle area of the elastic body part is concave and forms the support part corresponding to the user's cheek area.

The disclosure also discloses a breathing mask, which is configured to surround the user's nose and mouth and form a sealing area between the lower lip area and the nasal bridge area, or surround the user's nose and form a sealing area between the upper lip area and the nasal bridge area, and supply pressurized breathing gas to the user's airway, including:

A rigid member with an interface on the side far away from the user's face for accessing the breathing gas of the continuous positive airway pressure device, and with a flared joint on the side adjacent to the user's face, when worn by the user;

An elastic member that is in communication with the inner cavity of the rigid member and is fixedly connected to the flared joint, the side of the elastic member adjacent to the user's face at least partially abutting the user's nasal bridge area to form an elastic body part, and a support part connected to the elastic body part being provided on the side of the elastic member adjacent to the user's face; and A foam member, which is fixed to the support part and forms, together with the elastic member, a sealing surface for fitting the user's face;

The foam member includes a first surface that contacts the user's face and a second surface that is fixedly connected to the support part, and the angle R between the first surface and the second surface is between 0-80°; the cross-sectional angle a between the elastic body part and the support part is between 10-170°.

In one embodiment, the inner side of the support part is provided with a joint part connected to the inner side of the elastic body part, the joint part corresponding to the user's cheek area, and the width of the joint part is 0.3-5 mm.

In one embodiment, the rigid member is made of plastic material; the elastic member is made of silicone, rubber, thermoplastic elastomer, or silicone resin material; and the foam member is made of polyurethane foam, low-density polyether foam, ethylene-vinyl acetate foam, rubber foam, or latex material.

In one embodiment, the elastic member is connected to the rigid member's flared joint by an injection-molded connection, adhesive bonding or buckle connection; the foam member is fixed on the support part by molding, hot pressing, welding, or foaming, or the foam member is adhered to the support part by glue or tape, or the foam member is snapped onto the support part.

The disclosure also discloses a breathing mask, which is configured to surround the user's nose and mouth and form a sealing area between the lower lip area and the nasal bridge area, or surround the user's nose and form a sealing area between the upper lip area and the nasal bridge area, and supply pressurized breathing gas to the user's airway, including:

A rigid member with an interface on the side far away from the user's face for accessing the breathing gas of the continuous positive airway pressure device, and with a flared joint on the side adjacent to the user's face, when worn by the user;

An elastic member that is in communication with the inner cavity of the rigid member and is fixedly connected to the flared joint, the side of the elastic member adjacent to the user's face at least partially abutting the user's nasal bridge area to form an elastic body part, and a support part connected to the elastic body part being provided on the side of the elastic member adjacent to the user's face; and A foam member, which is fixed to the support part and forms, together with the elastic member, a sealing surface for fitting the user's face;

The elastic body part in contact with the face includes at least one thin area and at least one non-thin area, and the thickness of at least a part of the thin area is 7%-60% of the non-thin area thickness, the width of the support part is 2-40 mm.

In one embodiment, the upper thickness of the elastic member is 8-40 mm; the thickness of the foam member is 1-30 mm.

The disclosure discloses yet another breathing mask, which is configured to surround the user's nose and mouth and form a sealing area between the lower lip area and the nasal bridge area, or surround the user's nose and form a sealing area between the upper lip area and the nasal bridge area, and supply pressurized breathing gas to the user's airway, including:

A rigid member with an interface on the side far away from the user's face for accessing the breathing gas of the continuous positive airway pressure device, and with a flared joint on the side adjacent to the user's face, when worn by the user;

An elastic member, which is in communication with the inner cavity of the rigid member and is fixedly connected to the flared joint, and at least a part of it is configured to be in contact with the user's face during use; and A foam member, which is connected to the elastic member and together forms a sealing surface for fitting the user's face;

The elastic member has at least one thin area, the thickness of the thin area is between 0.2-2 mm;

The width of the foam member is 3-30 mm, or/and the width-to-thickness ratio of the foam member is 0.1-30, or/and the foam member has a non-continuous three-dimensional shape.

In one embodiment, the foam member has a twisted U-shaped structure in three-dimensional space.

In one embodiment, the foam member has a twisted inverted V-shaped structure in three-dimensional space.

In one embodiment, the foam member has a twisted and spaced inclined symmetrical extension structure in three-dimensional space.

In one embodiment, the cross-section of the foam member is a triangular, quadrilateral, pentagonal, or hexagonal structure; and the edge of the foam member near the user's face has a curved portion.

The breathing mask with a foam pad according to the disclosure has at least the following beneficial effects:

The elastic body part provided by the elastic member and the foam member together fit the user's face, ensuring the fit of the breathing mask with the user's nasal bridge area and ensuring the sealing effect; by fitting the foam member to the rest of the user's face, the uneven pressure caused by tightening the head strap on the user's face can be distributed, providing a uniform force on the user's face and improving the user's experience of wearing the breathing mask.

The foam member has good breathability, can absorb sweat and grease on the face during the night, keep the user's face dry, reduce the possibility of mask displacement, and ensure the sealing of the mask.

The elastic body part and the foam member are made of flexible materials, which can fit well with the user's face when subjected to pressure, ensuring the sealing effect and wearing comfort, and can adapt to and fit the faces of most users.

DETAILED DESCRIPTION

To make the above-mentioned objectives, features, and advantages of the present disclosure more apparent and easy to understand, a detailed description of specific embodiments of the present disclosure will be given below in conjunction with the accompanying drawings. Many specific details are set forth in the following description to provide a thorough understanding of the present disclosure. However, the present disclosure can be implemented in many other ways different from those described herein, and those skilled in the art can make similar improvements without departing from the spirit of the present disclosure, so the present disclosure is not limited by the specific embodiments disclosed below.

The present disclosure addresses the issue of traditional breathing masks that use non-breathable elastic materials such as silicone at the parts where the mask contacts the user's face. Due to large individual facial differences, the pressure exerted by the head strap and the pressure of the respiratory gas used for treatment can cause excessive local pressure on the user's face as it contacts the elastomer, leading to discomfort, red marks, and pressure sores. Additionally, the use of padding can lead to the problem of padding falling off easily. The present disclosure provides a sealing surface composed of elastic material and foam material at the parts where the breathing mask contacts the user's face, making the sealing surface at least in contact with the user's nasal bridge made of elastic material to avoid air leakage around the nasal bridge. The foam material is in contact with the remaining parts to distribute the force exerted on the user's face by the tightening of the head strap, making the force on the user's face uniform and improving the user's experience when wearing the breathing mask.

Furthermore, the breathing mask with a foam pad in this embodiment is configured to surround the user's nose and mouth, forming a sealing area between the lower lip area and the nasal bridge area, or to surround the user's nose and form a sealing area between the upper lip area and the nasal bridge area, supplying pressurized breathing gas to the user's airway. In other words, the breathing mask in this embodiment can be designed as a smaller size that only covers the user's nose and contacts the user's cheeks and upper lip area, providing pressurized breathing gas only through the user's nostrils to the user's airway. It can also be designed as a larger size that covers both the user's nose and mouth and contacts the user's cheeks and lower lip area, providing pressurized breathing gas through both the user's nostrils and mouth to the user's airway, meeting the needs of users with different usage habits and physiological conditions.

Figure 1:
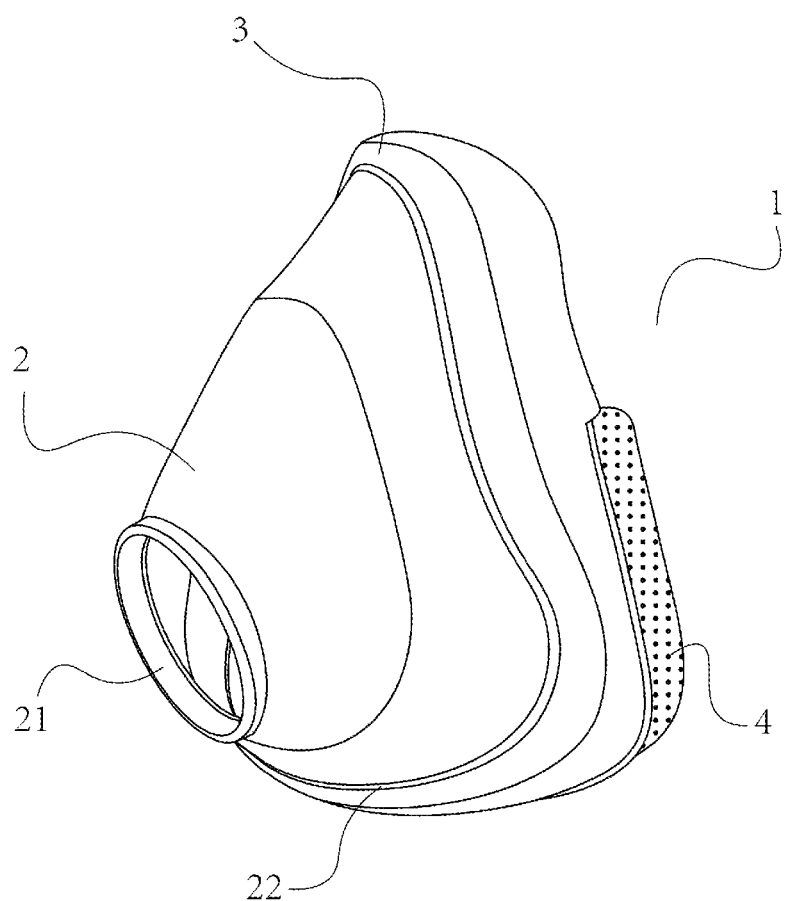
FIG. 1 is a structural schematic diagram of a breathing mask in an embodiment of the present disclosure.
Figure 2:
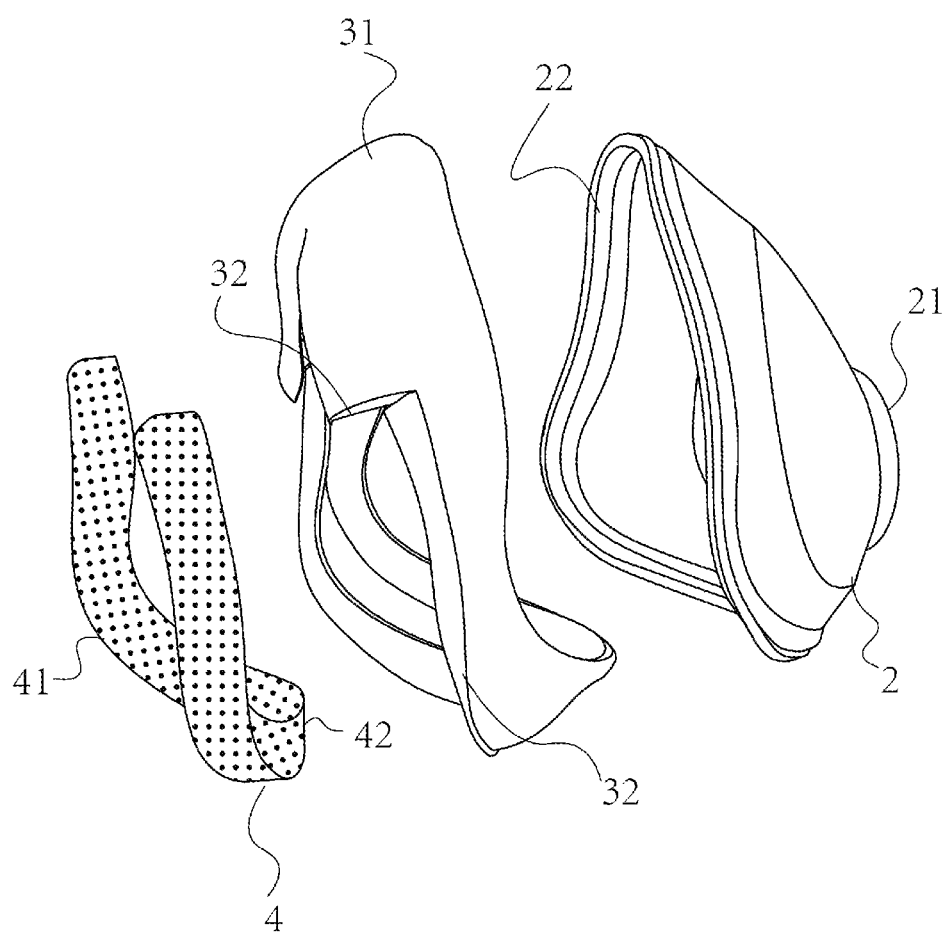
FIG. 2 is an exploded structure schematic diagram of the breathing mask in an embodiment of the present disclosure.
Figure 3:
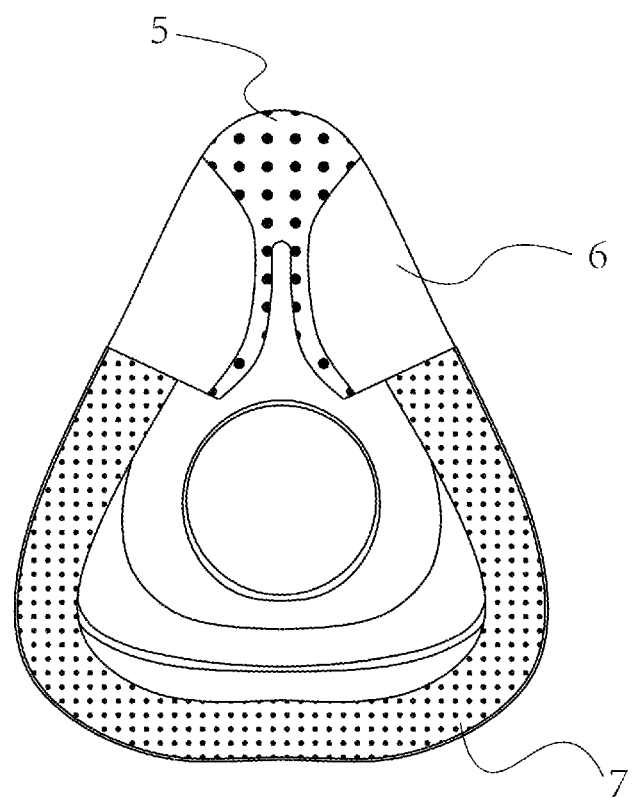
FIG. 3 is a regional division diagram of the breathing mask in an embodiment of the present disclosure.

Referring to FIGS. 1 to 3, a breathing mask 1 includes a rigid member 2, an elastic member 3, and a foam member 4. The rigid member 2 can be detachably connected to an external frame, which is equipped with a tighten-able head strap for securing the breathing mask 1 to the user's head. The interface of the rigid member 2 is used to connect to the continuous positive airway pressure device's breathing gas, the rigid member ensuring the shape of the breathing mask 1 and providing support for the elastic member 3. In this embodiment, the rigid member 2 can be made of transparent, opaque, or semi-transparent materials. Furthermore, the rigid member 2 is made of plastic material, such as hard plastic materials like polycarbonate, polyvinyl chloride, or polyethylene. On the side of the rigid member 2 away from the user's face, when worn by the user, there is an interface 21 for connecting to the continuous positive airway pressure device's breathing gas. This interface 21 is located in the middle of the front side of the rigid member 2 to ensure that the connection between the rigid member 2 and the external frame is evenly stressed, preventing the tube from dragging the rigid member 2 and causing the breathing mask 1 to become loose or fall off the user's face, thus ensuring the sealing of the breathing mask 1. On the side of the rigid member 2 close to the user's face, there is a flared joint 22, which is used to provide a joint part for the elastic member 3. In addition, the breathing mask 1 includes a nasal bridge part 5 corresponding to the user's nasal bridge area, a cheek area 6 corresponding to the user's cheek area, and a mouth part 7 corresponding to the user's mouth area.

Figure 7:
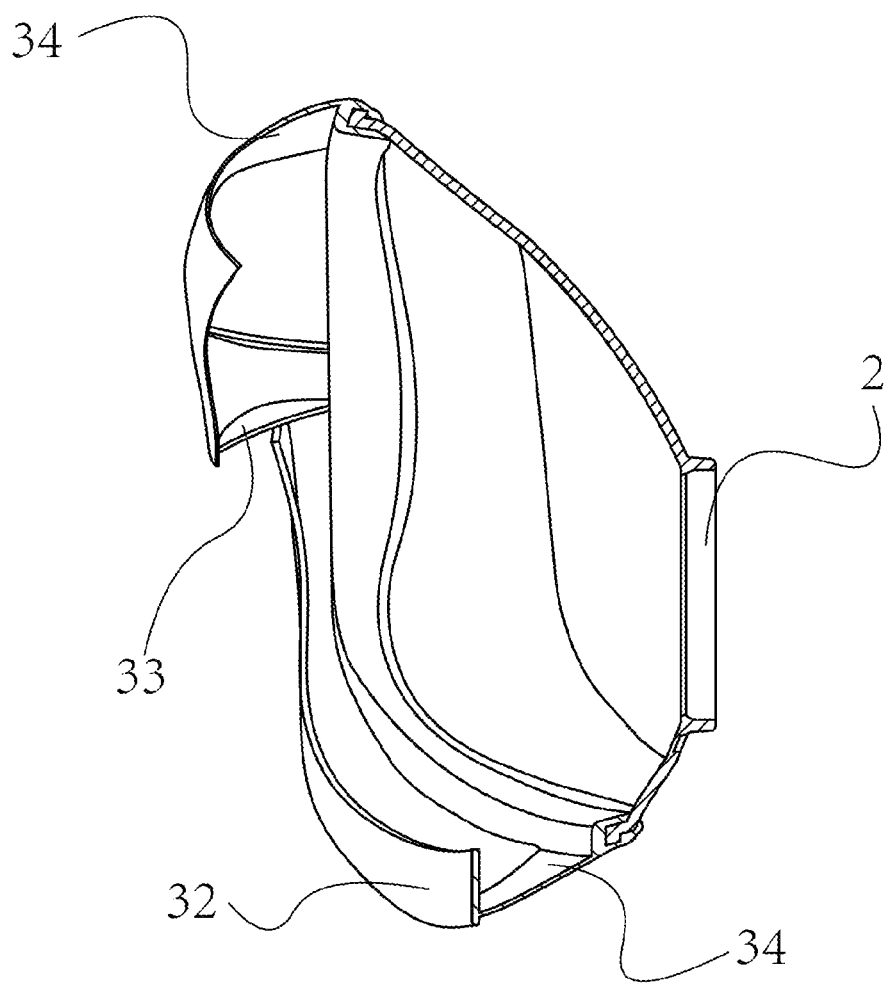
FIG. 7 is a cross-sectional view in the A-A direction of FIG. 4.

The elastic member 3 communicates with the inner cavity of the rigid member 2 and is fixedly connected to the flared joint 22, with the elastic member 3 and the edges of the flared joint 22 joined together. In this embodiment, the elastic member 3 is connected to the flared joint 22 of the rigid member 2 by an injection-molded connection (through a secondary injection molding process, the elastic member 3 and the rigid member 2 are formed as one single piece), adhesive bonding (such as adhesive), or buckle connection (by constructing a clip or use a buckle structure on the elastic member 3 and the rigid member 2 to join). Furthermore, the elastic member 3 is made of airtight, soft, and deformable materials, such as silicone, rubber, thermoplastic elastomers, or silicone resin materials. Further, referring to FIGS. 2, 4, and 7, at least part of the side of the elastic member 3 close to the user's face abuts the user's nasal bridge area to form an elastic body part 31, and the side of the elastic member 3 close to the user's face is provided with a support part 32 connected to the elastic body part 31. At least part of the elastic body part 31 contacts the user's nasal bridge area, so that it fits the user's nasal bridge area securely when the head strap is tightened to avoid air leakage around the nasal bridge area and ensure the sealing of the breathing mask 1; the support part 32 is used to support and connect the foam member 4, realizing the positioning of the foam member 4.

The foam member 4 is fixed to the support part 32 and forms a sealing surface for fitting the user's face together with the elastic member 3. In this embodiment, the foam member 4 is made of porous materials, such as polyurethane foam, low-density polyether foam, ethylene-vinyl acetate foam, rubber foam, or latex materials, with a density range of 10-100 kg/m3. Since the foam member 4 is a porous material, in order not to affect the therapeutic effect, the permeability of the foam member 4 is less than 50 L/min to avoid leakage of the breathing gas through the foam member 4. Further, the elastic member 3 and the foam member 4 are connected during use, and the foam member 4 is fixed to the support part 32 by molding, hot pressing, welding, or foaming, or the foam member 4 is glued or taped to the support part 32, or the foam member 4 is connected to the support part 32 by a buckle structure. In addition, the foam member 4 can also be fixed to the support part 32 of the elastic member 3 through other auxiliary accessories, such as clips or straps.

It should be noted that in this embodiment, the combination of the elastic body part 31 and the foam member 4 is used as the sealing surface because, when the entire sealing surface is made of elastic materials such as silicone, the airtight nature of silicone may cause some users to experience facial sweating and oiliness during use. This situation can lead to the displacement or weakening of the sealing performance of the breathing mask due to the movement of the user's head during sleep. This application combines the elastic body part 31 and the foam member 4 to achieve a sealing effect while fitting the nasal bridge with the elastic body part 31, and the foam member 4 has good air permeability and can absorb sweat and oil from the face during the night, keeping the user's face dry and reducing the likelihood of the breathing mask shifting, ensuring the sealing of the breathing mask.

When the sealing surface is designed as a foam structure, that is, the interface between the breathing mask and the user's face is a continuous annular foam, although it can allow users to be in full contact with comfortable foam material, in order to achieve good sealing at the bridge of the nose and ensure the user experience, the thickness of the foam at the bridge of the nose will be designed to be thinner than other areas and have a larger overhanging part. In this case, the nasal area of the breathing mask is compressed during use, causing foam tearing and damage, making the breathing mask unable to seal properly. This has also been confirmed in market feedback. Additionally, due to the large height difference between the bridge of the nose and the facial area, the nasal side area is prone to leakage, making it easy for the breathing gas to blow into the eyes through the gap during use, affecting the user experience. Therefore, in an embodiment, a non-breathable elastic material is still used at the nasal bridge of the breathing mask to prevent leakage of breathing gas. Compared to foam material, the use of elastic material in the nasal bridge area of the breathing mask prolongs the service life of the breathing mask, making it more durable, while foam material is used in the relatively flat areas of the cheeks and chin. Foam member 4 has smaller undulations and is not easily torn, which maximizes sealing and comfort while prolonging the service life of foam member 4. In this embodiment, by constructing the sealing surface of the breathing mask as a combination of two materials, better sealing performance and increased comfort can be achieved without affecting the main function of the product. The overall service life of the product is also greatly improved compared to prior products.

Figure 12:
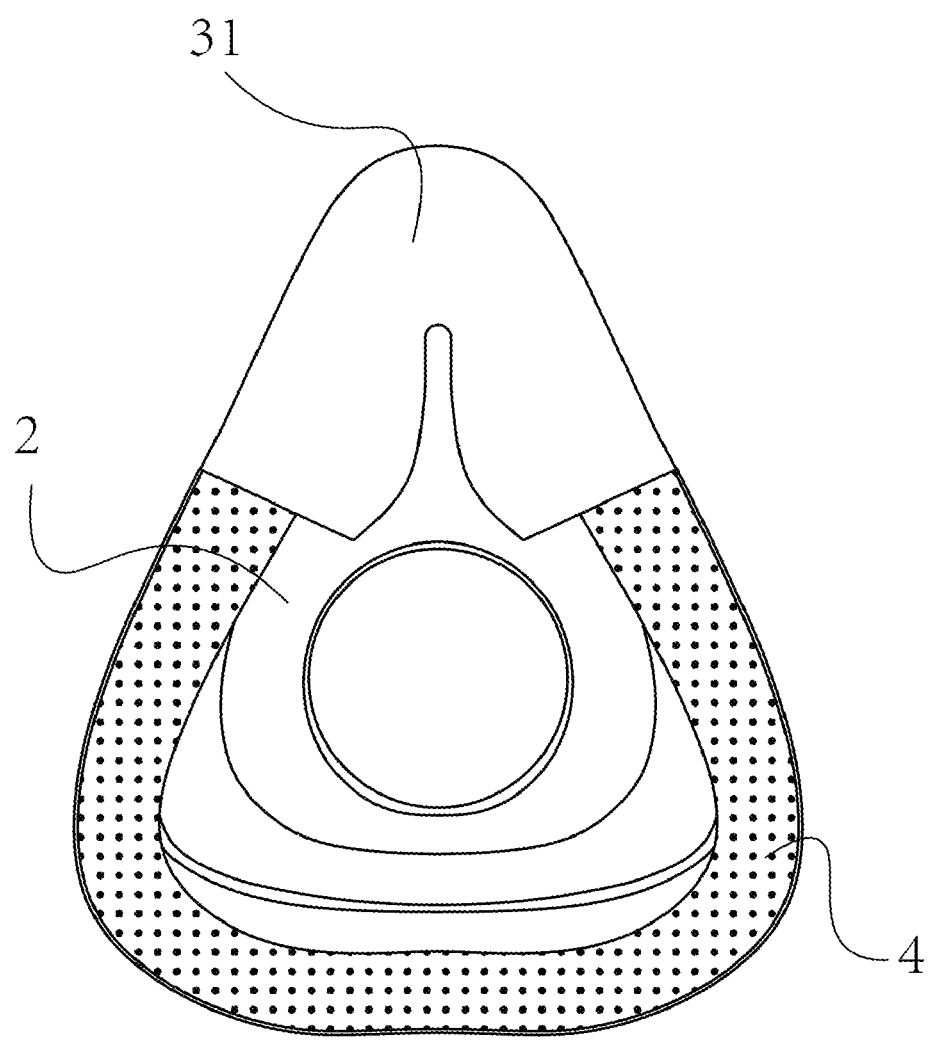
FIG. 12 is a rear view of the breathing mask in the embodiment shown in FIG. 1.
Figure 13:
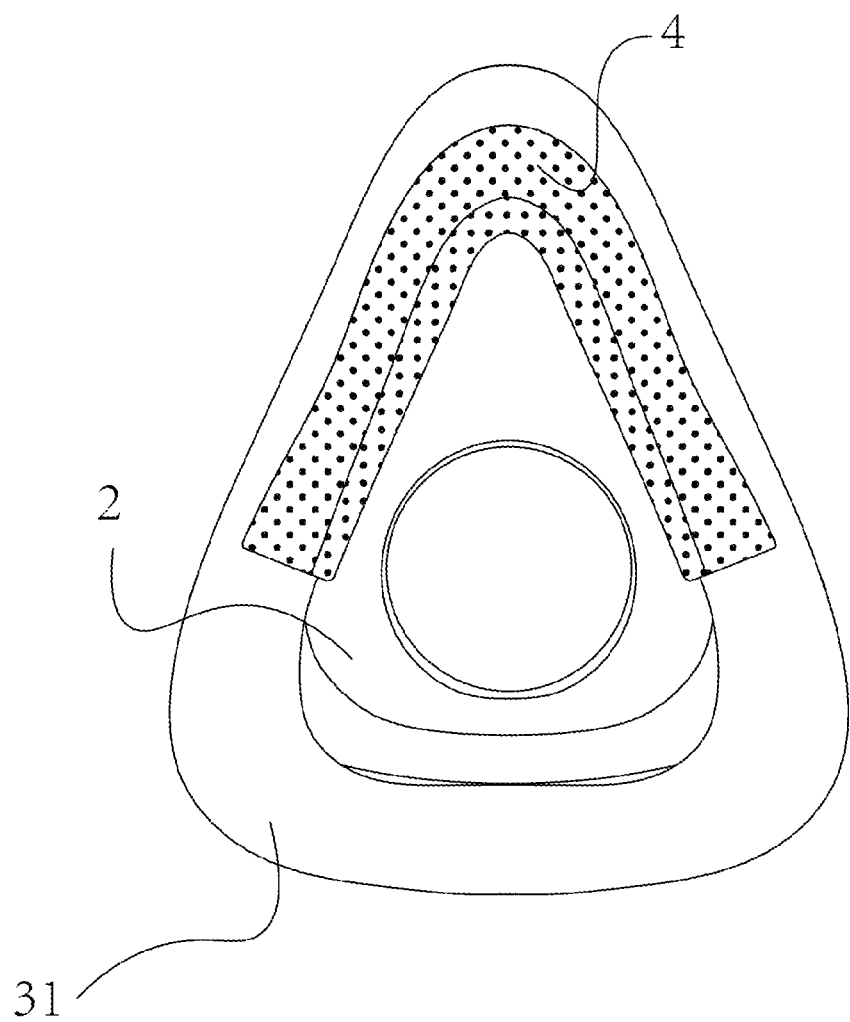
FIG. 13 is a rear view of the breathing mask in another embodiment of the present disclosure.
Figure 14:
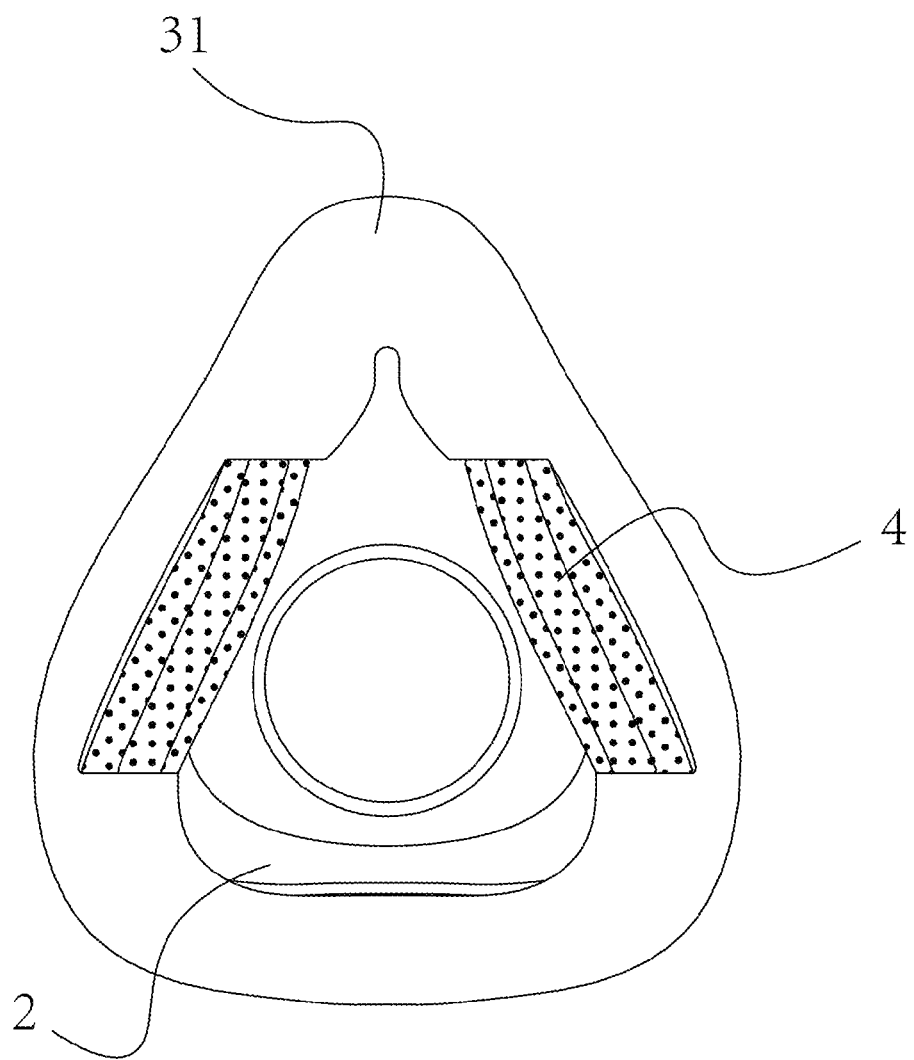
FIG. 14 is a rear view of the breathing mask in yet another embodiment of the present disclosure.

The breathing mask of the present disclosure includes various deformation structures. In the different deformation structures, the shape of the foam member 4 and the position of the foam member 4 on elastic member 3 can be different. In some cases, the elastic body part 31 on the elastic member 3 is at least in contact with the user's nasal bridge area to ensure the sealing of the breathing mask. Specifically, referring to FIGS. 1 and 12, in one embodiment, the elastic body part 31 corresponds to the user's nasal bridge area or/and cheek area, and the lower area of the elastic body part 31 is concave to form a support part 32 corresponding to the user's mouth area. Foam member 4 has a twisted U-shaped structure in a three-dimensional space, that is, foam member 4 is in contact with the user's cheeks and chin, or foam member 4 is in contact with the user's cheeks and upper lip area. In this case, the elastic body part 31 has an inverted V-shaped structure. Referring to FIG. 13, in another embodiment, the elastic body part 31 corresponds to the user's mouth area, and the inner upper area of the elastic body part 31 is concave to form a support part 32 corresponding to the user's nasal bridge area and cheek area. Foam member 4 has a twisted inverted V-shaped structure in a three-dimensional space, that is, elastic body part 31 has a circular structure and is in contact with the user's face, and foam member 4 is in contact with the user's nasal bridge area or/and cheek area. Referring to FIG. 14, in yet another embodiment, the elastic body part 31 corresponds to the user's nasal bridge area and mouth area, and the inner middle area of the elastic body part 31 is concave to form a support part 32 corresponding to the user's cheek area. Foam member 4 has a twisted and spaced symmetrical extension structure in a three-dimensional space, that is, foam member 4 includes two relatively arranged foam pieces, with the upper part of the two foam pieces being parallel, and the lower part of the two foam pieces bending away from the direction of the area between the two foam pieces. Foam member 4 has an overall symmetrical extension structure, and the elastic body part 31 has a circular structure and is in contact with the user's face, and foam member 4 with an inclined symmetrical extension structure is distributed on both sides of the user's alar area and in contact with the user's cheek area.

In some of the embodiments as discussed above, the foam member 4 has a twisted structure in the three-dimensional space, that is, the foam member 4 is a non-continuous three-dimensional structure, so that the shape of the side of the foam member 4 adjacent to the user's face conforms to the user's facial contours. Furthermore, in one embodiment, the elastic body part 31 in contact with the face includes at least one thin area 34 and at least one non-thin area, with the thickness of the thin area 34 ranging between 0.2-2 mm, and at least part of the thin area 34 being between 7%-60% of the thickness of the non-thin area. In this embodiment, the thin area 34 is located in at least one of the nose bridge part 5 or the mouth area of the breathing mask, allowing the thin area 34 to conform to the user's face under the influence of treatment pressure, thereby achieving a sealing effect. In this embodiment, the thin area 34 and non-thin area can be smoothly connected (with a gradual transition) or abruptly connected (with the joint part forming a step) . Additionally, when the foam part 4 is in a U-shaped structure or a symmetrical extending structure, the elastic body part 31 or the nose bridge part 5 corresponding to the breathing mask on the elastic body part 31 is constructed as a thin area 34 to accommodate the user's nose bridge, and the elastic body part 31 also has inwardly extending wings in the area corresponding to the nose bridge to fit both sides of the user's nose and prevent respiratory gas leakage.

Figure 4:
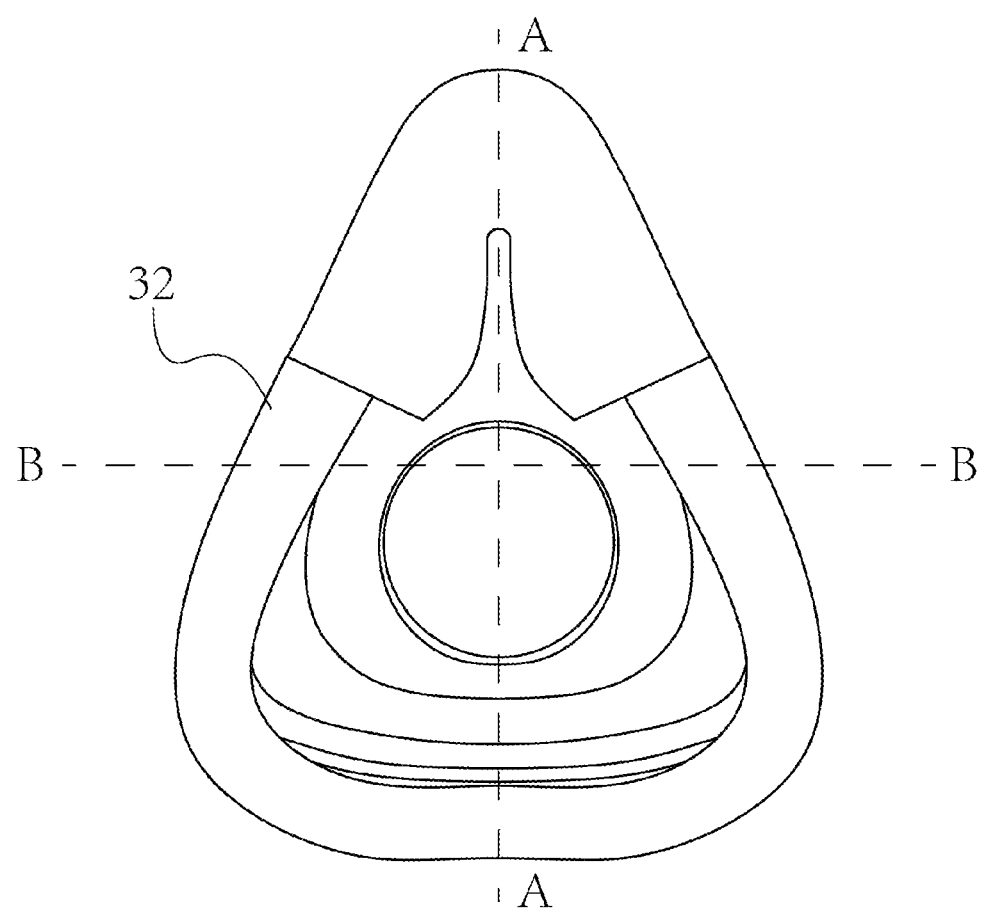
FIG. 4 is a structure schematic diagram of the connection between the rigid member and the elastic member in an embodiment of the present disclosure.
Figure 8:
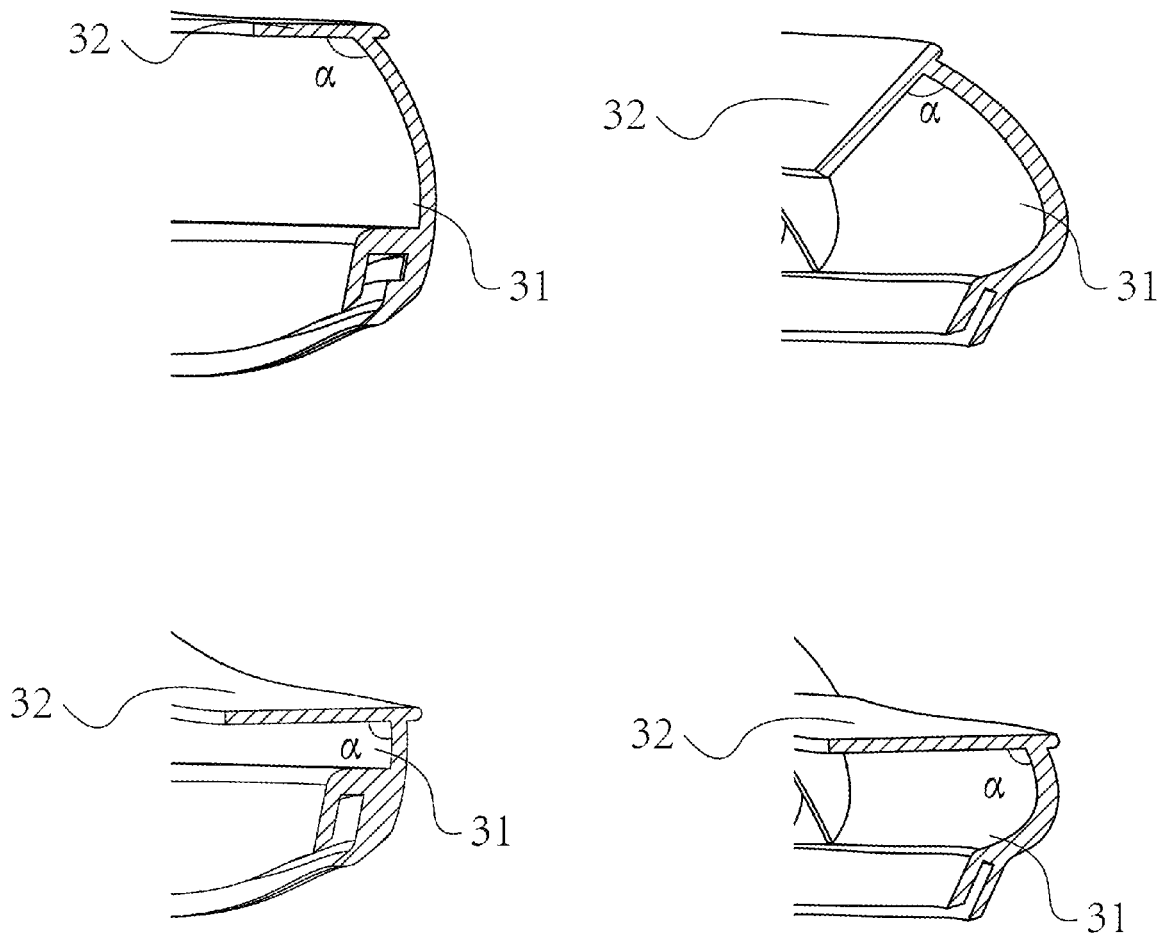
FIG. 8 is a structural diagram of the cross-section in the B-B direction of FIG. 4 under multiple embodiments.

To ensure that the elastic member 3 conforms to the face during use and has sufficient deformation space, and to avoid the user tightening the head strap causing the rigid member 2 to directly apply pressure to the face, the upper thickness of the elastic member 3 (i.e., the height between the edge of the elastic member 3 and the edge that the elastic member surrounds the rigid part) can be 8-40 mm. Further preferably, the minimum distance from the support part 32 to the surface of the rigid member 2 can be 8 mm. The cross-section formed by the elastic body part 31 and the support part 32 (i.e., the cross-section formed by the recess in the elastic body part 31) can be an approximately T-shaped structure or J-shaped structure. To adapt to the undulations of the user's face, the support part 32 of the elastic member 3 is on different horizontal planes, that is, the support part 32 of the elastic member 3 is twisted in the three-dimensional space and forms a three-dimensional curved surface. When the elastic body part 31 is in contact with the user's face, at least a portion of the area on the support part 32 is suspended (that is, at least a portion of the support part 32 is not supported, as shown in FIG. 8), and the support part 32 can be convex or concave relative to the elastic body part 31. Referring to FIGS. 4 and 8, considering the three-dimensional shape of the face, the angle a between the cross-section of the elastic body part 31 and the support part 32 can be between 10-170°, specifically, when the breathing mask is stationary, the maximum angle a between the cross-section of the elastic body part 31 and the support part 32 is 170°. To ensure the effective connection between the support part 32 and the foam member 4, the width of the support surface can be 2-40 mm; to ensure the supporting force of the elastic member 3, the inner side of the support part 32 is provided with a connecting part 33 connected to the inner side of the elastic body part 31, and the connecting part 33 can also be used to prevent the support part 32 from turning outward under treatment pressure. In this embodiment, the connecting part 33 corresponds to the user's cheek area, and the width of the connecting part can be between 0.3-5 mm.

Figure 5:
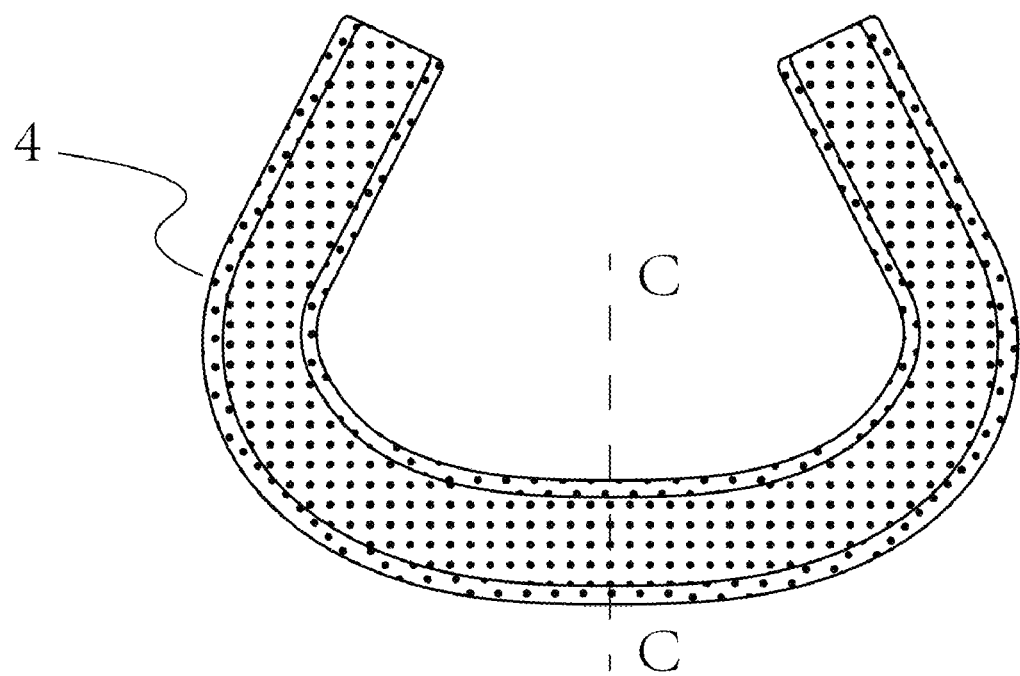
FIG. 5 is a main view of the foam member in an embodiment of the present disclosure.
Figure 6:
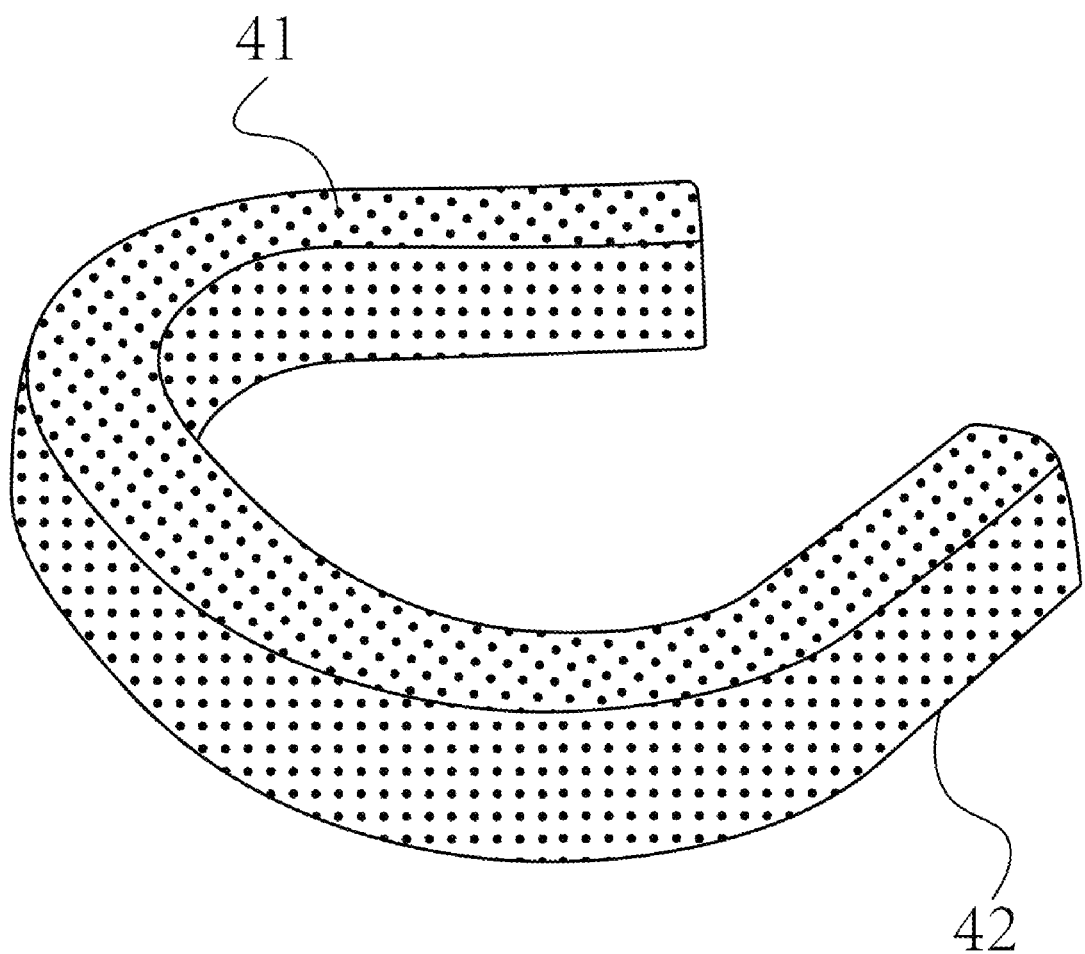
FIG. 6 is a three-dimensional diagram of the foam member in an embodiment of the present disclosure.
Figure 9:
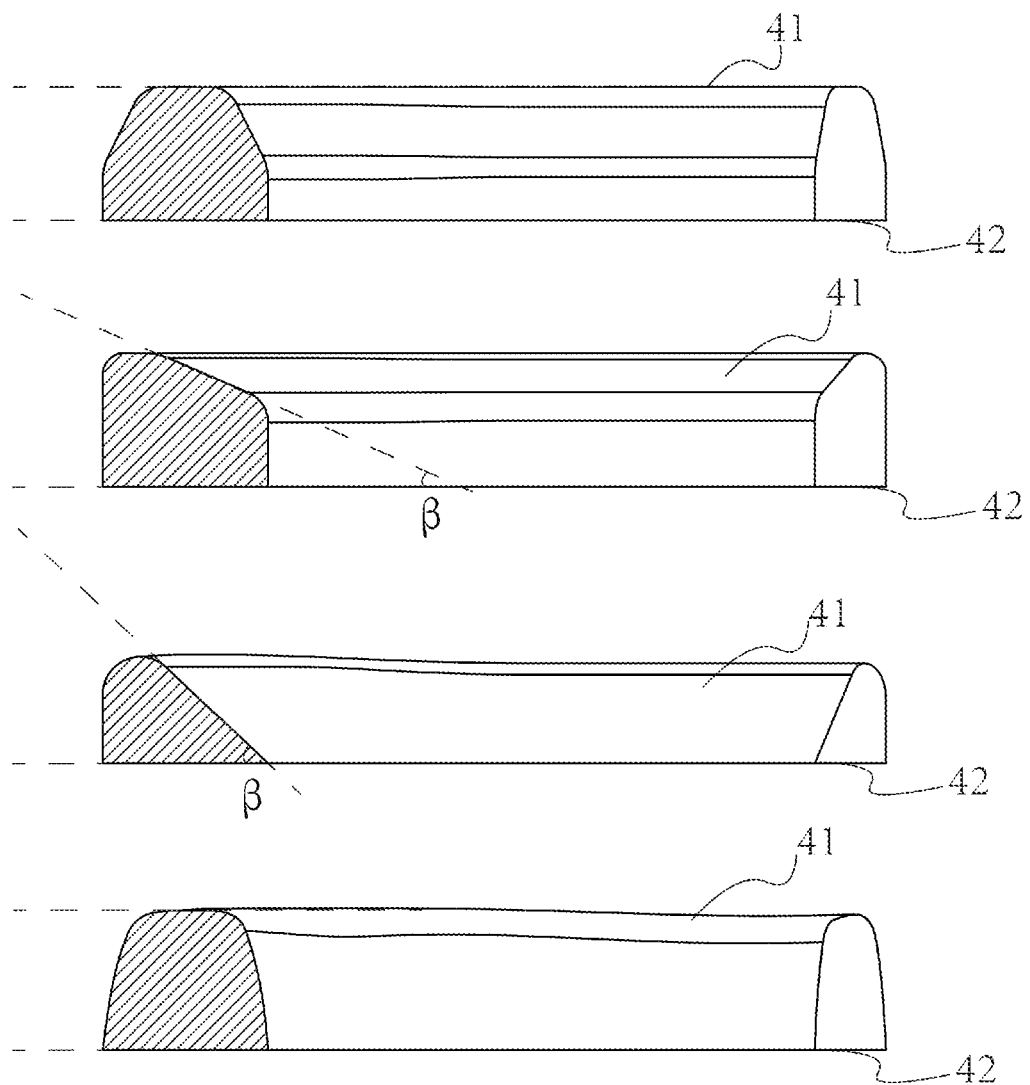
FIG. 9 is a structural diagram of the cross-section in the C-C direction of FIG. 5 under multiple embodiments.
Figure 10:
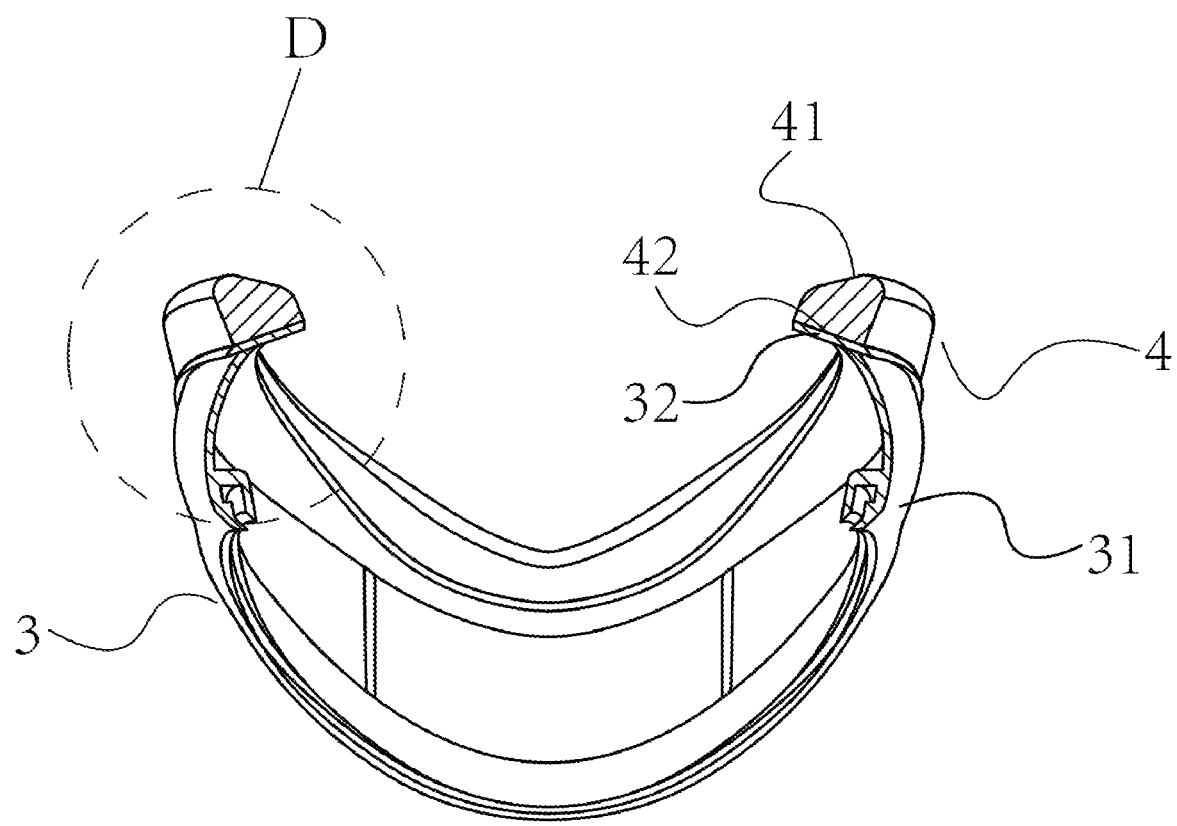
FIG. 10 is a sectional structure diagram of the connection between the support part and the foam member in an embodiment of the present disclosure.
Figure 11:
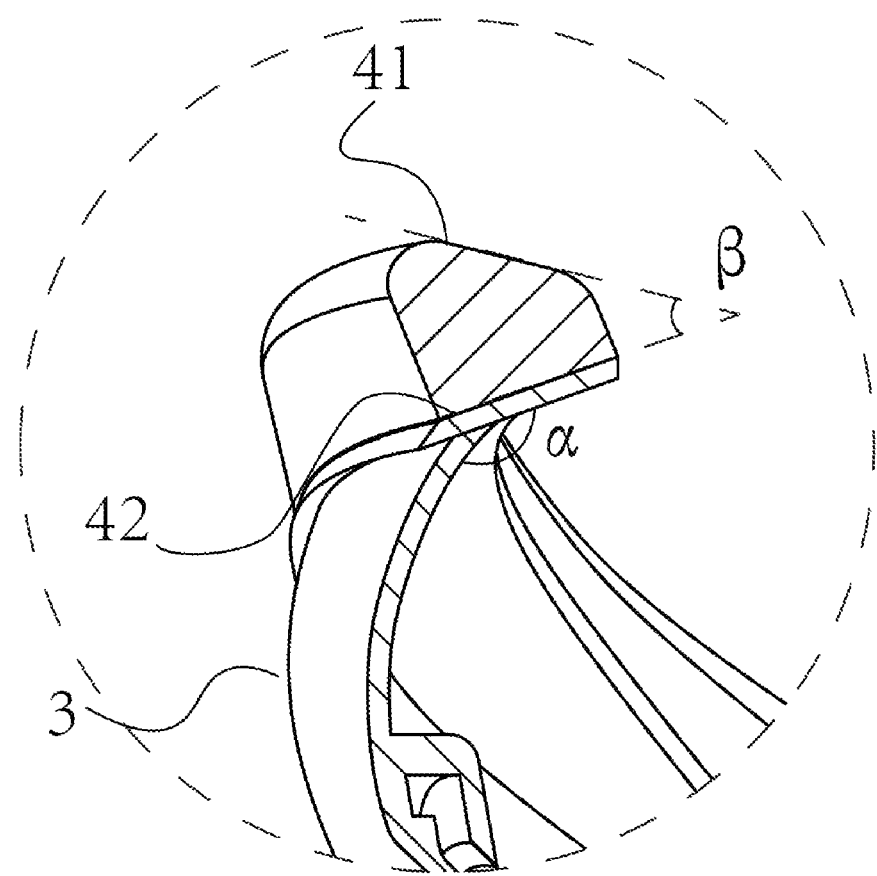
FIG. 11 is a partial enlarged schematic diagram of the D portion in the embodiment shown in FIG. 10.

Please referring to FIGS. 5, 6, and 9, the foam member 4 has a non-continuous three-dimensional shape, such as an arc or U-shaped structure. Foam member 4 includes a first surface 41 in contact with the user's face and a second surface 42 fixedly connected to the support part 32. Generally speaking, the second surface 42 is approximately a plane. The second surface 42 adapts to the curvature of the support part 32 of the elastic member 3 when connected. During use, the first surface 41 generally fits the contour of the face. The first surface 41 and the second surface 42 can be parallel, or they can form a certain angle as the foam member 4 moves towards the face. Preferably, please refer to FIGS. 10 and 11: In this embodiment, the angle between the first surface 41 and the second surface 42 can be between 0-80°. Furthermore, to fit the face, the first surface 41 of the foam member 4 remains horizontal or tilts inward, and the angle relative to the horizontal plane can be between 10-50°.

To provide a better user experience and prevent the user's face from scraping against the support part 32 during use, in one embodiment, the inner edge of the foam member 4 is flush with the inner edge of the support part 32, or the inner edge of the foam member 4 protrudes beyond the inner edge of the support part 32. In addition, the inner ring of the foam part 4 needs to have enough space to accommodate the user's nose or mouth, and the width of the foam member 4 can be between 3-30 mm. To provide a comfortable and stable support for the user's face, the thickness of the foam part 4 can be between 1-30 mm, and the width-to-thickness ratio of the foam member 4 can be between 0.1-30. The cross-section of the foam member 4 is a triangular, quadrilateral, pentagonal, or hexagonal structure. For better comfort, the edge of the foam member 4 near the user's face side has an arc portion.

The following are several structures of a breathing mask with a foam pad according to the present disclosure, illustrated with specific examples.

Embodiment 1

The breathing mask 1 with a foam pad in this embodiment is configured to surround the user's nose and mouth and form a sealing area between the lower lip area and the nasal bridge area, or surround the user's nose and form a sealing area between the upper lip area and the nasal bridge area, and supply pressurized breathing gas to the user's airway. The mask includes a rigid member 2, an elastic member 3, and a foam member 4. The side of the rigid member 2 away from the user's face is provided with an interface 21 for accessing the breathing gas of the continuous positive airway pressure device. The side of the rigid member 2 close to the user's face is provided with a flared joint 22. The elastic member 3 communicates with the inner cavity of the rigid member 2 and is fixedly connected to the flared joint 22. The side of the elastic member 3 near the user's face is at least partially in contact with the user's nasal bridge area to form an elastic body part 31, and the side of the elastic member 3 near the user's face is provided with a support part 32 connected to the elastic body part 31. The foam member 4 is fixed to the support part 32 and forms a sealing surface with the elastic part 3 for fitting the user's face. The inner edge of the foam member 4 is flush with the inner edge of the support part 32, or the inner edge of the foam member 4 protrudes beyond the inner edge of the support part 32.

The above embodiment can include three variations. In the first variation, the elastic body part 31 corresponds to the user's nasal bridge area or/and cheek area, and the lower area of the elastic body part 31 is concave to form a support part 32 corresponding to the user's mouth area. In the second variation, the elastic body part 31 corresponds to the user's mouth area, and the inner upper area of the elastic body part 31 is concave to form a support part 32 corresponding to the user's nasal bridge area or/and cheek area. In the third variation, the elastic body part 31 corresponds to the user's nasal bridge area and mouth area, and the inner middle area of the elastic body part 31 is concave to form a support part 32 corresponding to the user's cheek area.

Embodiment 2

The breathing mask 1 with a foam pad in this embodiment is configured to surround the user's nose and mouth and form a sealing area between the lower lip area and the nasal bridge area, or surround the user's nose and form a sealing area between the upper lip area and the nasal bridge area, and supply pressurized breathing gas to the user's airway. The mask includes a rigid member 2, an elastic member 3, and a foam member 4. The side of the rigid member 2 away from the user's face is provided with an interface 21 for accessing the breathing gas of the continuous positive airway pressure device. The side of the rigid member 2 close to the user's face is provided with a flared joint 22. The elastic member 3 communicates with the inner cavity of the rigid member 2 and is fixedly connected to the flared joint 22. The side of the elastic member 3 near the user's face is at least partially in contact with the user's nasal bridge area to form an elastic body part member 31, and the side of the elastic member 3 near the user's face is provided with a support part 32 connected to the elastic body part 31. The foam member 4 is fixed to the support part 32 and forms a sealing surface with the elastic member 3 for fitting the user's face. The foam member 4 includes a first surface 41 in contact with the user's face and a second surface 42 fixedly connected to the support part 32, and the angle between the first surface 41 and the second surface 42 can be between 0-80°; the cross-sectional angle a between the elastic body part 31 and the support part 32 can be between 10-170°.

In the above embodiment, the inner side of the support part 32 is provided with a joint part 33 connected to the inner side of the elastic body part 31, and the joint part 33 corresponds to the user's cheek area, with a width between 0.3-5 mm. The rigid member 2 is made of plastic material; the elastic member 3 is made of silicone, rubber, thermoplastic elastomers, or silicone resin materials; the foam member 4 is made of polyurethane foam, low-density polyether foam, ethylene-vinyl acetate foam, rubber foam, or latex materials. The elastic member 3 is connected to the flared joint 22 of the rigid member 2 by an injection-molded connection, adhesive bonding, or buckle connection; the foam member 4 is fixed to the support part 32 by molding, hot pressing, welding, or foaming methods, or the foam member 4 is adhered to the support part 32 with glue or adhesive tape, or the foam member 4 is buckle-connected to the support part 32.

Embodiment 3

The breathing mask 1 with a foam pad in this embodiment is configured to surround the user's nose and mouth and form a sealing area between the lower lip area and the nasal bridge area, or surround the user's nose and form a sealing area between the upper lip area and the nasal bridge area, and supply pressurized breathing gas to the user's airway. The mask includes a rigid member 2, an elastic member 3, and a foam member 4. The side of the rigid member 2 away from the user's face is provided with an interface 21 for accessing the breathing gas of the continuous positive airway pressure device. The side of the rigid member 2 close to the user's face is provided with a flared joint 22. The elastic member 3 communicates with the inner cavity of the rigid member 2 and is fixedly connected to the flared joint 22. The side of the elastic member 3 near the user's face is at least partially in contact with the user's nasal bridge area to form an elastic body part member 31, and the side of the elastic member 3 near the user's face is provided with a support part 32 connected to the elastic body part 31. The foam member 4 is fixed to the support part 32 and forms a sealing surface with the elastic member 3 for fitting the user's face. The elastic body part 31 in contact with the face includes at least one thin area 34 and at least one non-thin area, and the thickness of at least some of the thin areas 34 can be between 7%-60% of the non-thin area thickness, the width of the support part 32 being between 2-40 mm.

In the above embodiment, the upper thickness of the elastic member 3 can be between 8-40 mm; the thickness of the foam member 4 can be between 1-30 mm.

Embodiment 4

The breathing mask 1 with a foam pad in this embodiment is configured to surround the user's nose and mouth and form a sealing area between the lower lip area and the nasal bridge area, or surround the user's nose and form a sealing area between the upper lip area and the nasal bridge area, and supply pressurized breathing gas to the user's airway. The mask includes a rigid member 2, an elastic member 3, and a foam member 4. The side of the rigid member 2 away from the user's face is provided with an interface 21 for accessing the breathing gas of the continuous positive airway pressure device. The side of the rigid member 2 close to the user's face is provided with a flared joint 22. The elastic member 3 communicates with the inner cavity of the rigid member 2 and is fixedly connected to the flared joint 22, and at least a part of the elastic member 3 is configured to be in contact with the user's face during use. The foam member 4 is connected to the elastic member 3 and together they form a sealing surface for fitting the user's face. The elastic member 3 has at least one thin area with a thickness between 0.2-2 mm; the width of the foam member 4 can be between 3-30 mm, and/or the width-to-thickness ratio of the foam member 4 can be between 0.1-30, and/or the foam member 4 has a non-continuous three-dimensional shape.

The above embodiment can include three variations: 1. The foam member 4 has a twisted U-shaped structure in a three-dimensional space; 2. The foam member 4 has a twisted inverted V-shaped structure in a three-dimensional space; 3. The foam member 4 has a twisted and spaced inclined symmetrical extension structure in a three-dimensional space. In addition, the cross-section of the foam member 4 can be a triangular, quadrilateral, pentagonal, or hexagonal structure; and the edge of the foam member 4 close to the user's face side has an arcuate portion.

Furthermore, the technical features of each of the embodiments described above can be combined as needed to obtain a breathing mask 1 including all or part of the technical features.

The breathing mask 1 with a foam pad according to the present disclosure has at least the following beneficial effects A) The elastic body part 31 provided by the elastic part 3 and the foam part 4 together contact the user's face. The elastic body part 31 ensures that the breathing mask 1 fits the user's nasal bridge area, ensuring a good seal. By fitting the foam part 4 to the rest of the user's face, it can distribute the uneven pressure caused by tightening the head strap, making the force applied to the user's face more uniform, and improving the user's experience of wearing the breathing mask 1.

B) The foam part 4 has good breathability and can absorb sweat and grease from the face during the night, keeping the user's face dry and reducing the possibility of mask displacement, ensuring the sealing of the mask.

C) The elastic body part 31 and the foam part 4 are made of flexible materials, which can fit well with the user's face when being squeezed. While ensuring sealing effectiveness and wearing comfort, they can adapt to and fit the faces of most users.

Aspects

Any of Aspects 1-5 can be combined with any of Aspects 6-20, any of Aspects 6-10 can be combined with any of Aspects 1-5 and 11-20, any of Aspects 11-14 can be combined with any of Aspects 1-10 and 15-20, and any of Aspects 15-20 can be combined with any of Aspects 1-14.

Aspect 1: A breathing mask configured to surround a user's nose and mouth to form a sealing area between a lower lip area and a nasal bridge area, or to surround the user's nose to form a sealing area between an upper lip area and the nasal bridge area, and supply pressurized breathing gas to a user's airway, the breathing mask comprising: a rigid member with an interface on a side away from a user's face for accessing breathing gas of a continuous positive airway pressure device, and with a flared joint on a side adjacent to the user's face, when worn by a user; an elastic member that is in communication with an inner cavity of the rigid member and is fixedly connected to the flared joint, a side of the elastic member adjacent to the user's face at least partially abutting the user's nasal bridge area to form an elastic body part, and a support part connected to the elastic body part being provided on the side of the elastic member adjacent to the user's face; and a foam member that is fixed to the support part and, together with the elastic member, is configured to form a sealing surface for fitting the user's face, wherein an inner edge of the foam member is flush with an inner edge of the support part, or the inner edge of the foam member protrudes from the inner edge of the support part.

Aspect 2: The breathing mask according to Aspect 1, wherein the elastic body part corresponds to the user's nasal bridge area and/or a cheek area, and a lower area of the elastic body part is concave and forms the support part corresponding to the user's mouth.

Aspect 3: The breathing mask according to any of Aspects 1-2, wherein the elastic body part corresponds to the user's mouth, and an inner upper area of the elastic body part is concave and forms the support part corresponding to the user's nasal bridge area and/or a cheek area.

Aspect 4: The breathing mask according any of Aspects 1-3, wherein the elastic body part corresponds to the user's nasal bridge area and the mouth, and an inner middle area of the elastic body part is concave and forms the support part corresponding to a cheek area of the user.

Aspect 5: The breathing mask according to any of Aspects 1-4, wherein at least a portion of the support part is suspended, when worn by the user.

Aspect 6: A breathing mask configured to surround a user's nose and mouth to form a sealing area between a lower lip area and a nasal bridge area, or to surround the user's nose to form a sealing area between an upper lip area and the nasal bridge area, and supply pressurized breathing gas to a user's airway, the breathing mask comprising: a rigid member with an interface on a side away from a user's face for accessing the breathing gas of a continuous positive airway pressure device, and with a flared joint on a side adjacent to the user's face, when worn by a user; an elastic member that is in communication with an inner cavity of the rigid member and is fixedly connected to the flared joint, a side of the elastic member adjacent to the user's face at least partially abutting the user's nasal bridge area to form an elastic body part, and a support part connected to the elastic body part being provided on the side of the elastic member adjacent to the user's face; and a foam member, which is fixed to the support part and together with the elastic member is configured to form a sealing surface for fitting the user's face, wherein the foam member includes a first surface that is configured to contact the user's face and a second surface that is fixedly connected to the support part, and an angle β between the first surface and the second surface is between 0-80°, and a cross-sectional angle α between the elastic body part and the support part is between 10-170°.

Aspect 7: The breathing mask according to Aspect 6, wherein an inner side of the support part is provided with a joint part connected to an inner side of the elastic body part, the joint part corresponding to a user's cheek area, and a width of the joint part is between 0.3-5 mm.

Aspect 8: The breathing mask according to any of Aspects 6-7, wherein the rigid member is made of plastic material, the elastic member is made of silicone, rubber, thermoplastic elastomer, or silicone resin material, and the foam member is made of polyurethane foam, low-density polyether foam, ethylene-vinyl acetate foam, rubber foam, or latex material.

Aspect 9: The breathing mask according to any of Aspects 6-8, wherein the elastic member is connected to the flared joint of the rigid member by an injection-molded connection, adhesive bonding, or buckle connection, the foam member is fixed on the support part by molding, hot pressing, welding, or foaming, or the foam member is adhered to the support part by glue or tape, or the foam member is buckle-connected to the support part.

Aspect 10: The breathing mask according to any of Aspects 6-9, wherein a density range of the foam member is at or between 10-100 Kg/m3.

Aspect 11: A breathing mask configured to surround a user's nose and mouth to form a sealing area between a lower lip area and a nasal bridge area or to surround the user's nose to form a sealing area between an upper lip area and the nasal bridge area, and supply pressurized breathing gas to a user's airway, the breathing mask including: a rigid member with an interface on a side away from a user's face for accessing the breathing gas of a continuous positive airway pressure device, and with a flared joint on a side adjacent to the user's face, when worn by a user; an elastic member that is in communication with an inner cavity of the rigid member and is fixedly connected to the flared joint, a side of the elastic member adjacent to the user's face configured to at least partially abut the user's nasal bridge area to form an elastic body part, and a support part connected to the elastic body part being provided on the side of the elastic member adjacent to the user's face; and a foam member, which is fixed to the support part and together with the elastic member is configured to form a sealing surface for fitting the user's face, wherein the elastic body part in contact with the user's face includes at least one thin area and at least one non-thin area, and a thickness of at least a part of the thin area is 7%-60% of a thickness of the non-thin area, and a width of the support part is between 2-40 mm.

Aspect 12: The breathing mask according to Aspect 11, wherein a height of an upper thickness of the elastic member is between 8-40 mm, and the thickness of the foam member is between 1-30 mm.

Aspect 13: The breathing mask according to any of Aspects 11-12, wherein the thickness of the thin area of the elastic member is 0.2-2 mm.

Aspect 14: The breathing mask according to any of Aspects 11-13, wherein the thin area of the elastic member is smoothly connected with the non-thin area.

Aspect 15: A breathing mask configured to surround a user's nose and mouth to form a sealing area between a lower lip area and a nasal bridge area, or surround the user's nose to form a sealing area between an upper lip area and the nasal bridge area, and supply pressurized breathing gas to a user's airway, the breathing mask comprising: a rigid member with an interface on a side away from a user's face for accessing the breathing gas of a continuous positive airway pressure device, and with a flared joint on a side adjacent to the user's face, when worn by a user; an elastic member, which is in communication with an inner cavity of the rigid member and is fixedly connected to the flared joint, and at least a part of the elastic member is configured to be in contact with the user's face during use; and a foam member, which is connected to the elastic member and together is configured to form a sealing surface for fitting the user's face, wherein the elastic member has at least one thin area, and a thickness of the thin area is between 0.2-2 mm, and wherein a width of the foam member is between 3-30 mm, and/or a width-to-thickness ratio of the foam member is between 0.1-30, and/or the foam member is a non-continuous three-dimensional shape.

Aspect 16: The breathing mask according to Aspect 15, wherein the foam member has a twisted U-shaped structure in a three-dimensional space.

Aspect 17: The breathing mask according to any of Aspects 15-16, wherein the foam member has a twisted inverted V-shaped structure in a three-dimensional space.

Aspect 18: The breathing mask according to any of Aspects 15-17, wherein the foam member has a twisted and spaced inclined symmetrical extension structure in a three-dimensional space.

Aspect 19: The breathing mask according to any of Aspects 15-18, wherein a cross-section of the foam member is a triangular, quadrilateral, pentagonal, or hexagonal structure; and an edge of the foam member near the user's face has a curved portion.

Aspect 20: The breathing mask according to any of Aspects 15-19, wherein a permeability of the foam member is less than 50 L/min.

The technical features of the above-described embodiments can be combined in any way. To simplify the description, not all possible combinations of the technical features in the above embodiments have been described. However, as long as these combinations of technical features do not present contradictions, they should be considered within the scope of this disclosure.

The above-described embodiments only express several implementation methods of the present disclosure, and their descriptions are more specific and detailed, but this should not be understood as limiting the scope of the patent. It should be pointed out that, for those skilled in the art, several modifications and improvements can be made without departing from the concept of the present disclosure, and these are all within the scope of protection of the present disclosure. Therefore, the scope of protection of the patent should be determined by the attached claims.

The invention claimed is:

1. A breathing mask configured to surround a user's nose and mouth to form a sealing area between a lower lip area and a nasal bridge area, or to surround the user's nose to form a sealing area between an upper lip area and the nasal bridge area, and supply pressurized breathing gas to a user's airway, the breathing mask comprising:
    a rigid member with an interface on a side away from a user's face for accessing breathing gas of a continuous positive airway pressure device, and with a flared joint on a side adjacent to the user's face, when worn by a user;
    an elastic member that is in communication with an inner cavity of the rigid member and is fixedly connected to the flared joint, the elastic member comprising an elastic body part adjacent to the user's face at least partially abutting the user's nasal bridge area, wherein the elastic body part includes an upper area that at least partially abuts the user's nasal bridge area and a lower area forming a support part provided on a side of the elastic member adjacent to the user's face; and
    a foam member that is fixed to the support part, such that the foam member is aligned with the upper area of the elastic body part of the elastic member to form a sealing surface for fitting the user's face in the sealing area,
    wherein an inner edge of the foam member is flush with an inner edge of the support part, or the inner edge of the foam member protrudes from the inner edge of the support part.

2. The breathing mask according to claim 1, wherein the elastic body part corresponds to the user's nasal bridge area and/or a cheek area, and a lower area of the elastic body part is concave and forms the support part corresponding to the user's mouth.

3. The breathing mask according to claim 1, wherein the elastic body part corresponds to the user's mouth, and an inner upper area of the elastic body part is concave and forms the support part corresponding to the user's nasal bridge area and/or a cheek area.

4. The breathing mask according to claim 1, wherein the elastic body part corresponds to the user's nasal bridge area and the mouth, and an inner middle area of the elastic body part is concave and forms the support part corresponding to a cheek area of the user.

5. The breathing mask according to claim 1, wherein at least a portion of the support part is suspended, when worn by the user.

6. A breathing mask configured to surround a user's nose and mouth to form a sealing area between a lower lip area and a nasal bridge area, or to surround the user's nose to form a sealing area between an upper lip area and the nasal bridge area, and supply pressurized breathing gas to a user's airway, the breathing mask comprising:
    a rigid member with an interface on a side away from a user's face for accessing the breathing gas of a continuous positive airway pressure device, and with a flared joint on a side adjacent to the user's face, when worn by a user;
    an elastic member that is in communication with an inner cavity of the rigid member and is fixedly connected to the flared joint, the elastic member comprising an elastic body part adjacent to the user's face at least partially abutting the user's nasal bridge area, wherein the elastic body part includes an upper area that at least partially abuts the user's nasal bridge area and a lower area forming a support part provided on a side of the elastic member adjacent to the user's face; and
    a foam member, which is fixed to the support part such that the foam member is aligned with the upper area of the elastic body part of the elastic member to form a sealing surface for fitting the user's face in the sealing area,
    wherein the foam member includes a first surface that is configured to contact the user's face and a second surface that is fixedly connected to the support part, and an angle β between the first surface and the second surface is between 0-80°, and a cross-sectional angle α between the elastic body part and the support part is between 10-170°.

7. The breathing mask according to claim 6, wherein an inner side of the support part is provided with a joint part connected to an inner side of the elastic body part, the joint part corresponding to a user's cheek area, and a width of the joint part is between 0.3-5 mm.

8. The breathing mask according to claim 6, wherein the rigid member is made of plastic material, the elastic member is made of silicone, rubber, thermoplastic elastomer, or silicone resin material, and the foam member is made of polyurethane foam, low-density polyether foam, ethylene-vinyl acetate foam, rubber foam, or latex material.

9. The breathing mask according to claim 6, wherein the elastic member is connected to the flared joint of the rigid member by an injection-molded connection, adhesive bonding, or buckle connection, the foam member is fixed on the support part by molding, hot pressing, welding, or foaming, or the foam member is adhered to the support part by glue or tape, or the foam member is buckle-connected to the support part.

10. The breathing mask according to claim 6, wherein a density range of the foam member is at or between 10-100 Kg/m3.

11. A breathing mask configured to surround a user's nose and mouth to form a sealing area between a lower lip area and a nasal bridge area or to surround the user's nose to form a sealing area between an upper lip area and the nasal bridge area, and supply pressurized breathing gas to a user's airway, the breathing mask including:
    a rigid member with an interface on a side away from a user's face for accessing the breathing gas of a continuous positive airway pressure device, and with a flared joint on a side adjacent to the user's face, when worn by a user;
    an elastic member that is in communication with an inner cavity of the rigid member and is fixedly connected to the flared joint, the elastic member comprising an elastic body part adjacent to the user's face configured to at least partially abut the user's nasal bridge area, wherein the elastic body part includes an upper area that at least partially abuts the user's nasal bridge area and a lower area forming a support part provided on a side of the elastic member adjacent to the user's face; and
    a foam member, which is fixed to the support part such that the foam member is aligned with the upper area of the elastic body part of the elastic member to form a sealing surface for fitting the user's face in the sealing area,
    wherein the elastic body part in contact with the user's face includes at least one thin area and at least one non-thin area, and a thickness of at least a part of the thin area is 7%-60% of a thickness of the non-thin area, and a width of the support part is between 2-40 mm.

12. The breathing mask according to claim 11, wherein a height of an upper thickness of the elastic member is between 8-40 mm, and the thickness of the foam member is between 1-30 mm.

13. The breathing mask according to claim 11, wherein the thickness of the thin area of the elastic member is 0.2-2 mm.

14. The breathing mask according to claim 11, wherein the thin area of the elastic member is smoothly connected with the non-thin area.

15. A breathing mask configured to surround a user's nose and mouth to form a sealing area between a lower lip area and a nasal bridge area, or surround the user's nose to form a sealing area between an upper lip area and the nasal bridge area, and supply pressurized breathing gas to a user's airway, the breathing mask comprising:
- a rigid member with an interface on a side away from a user's face for accessing the breathing gas of a continuous positive airway pressure device, and with a flared joint on a side adjacent to the user's face, when worn by a user;
- an elastic member, which is in communication with an inner cavity of the rigid member and is fixedly connected to the flared joint, and at least a part of the elastic member is configured to be in contact with the user's face during use; and
- a foam member, which is connected to the elastic member such that the foam member is aligned with the part of the elastic member configured to be in contact with the user's face during use to form a sealing surface for fitting the user's face in the sealing area,
- wherein the elastic member has at least one thin area, and a thickness of the thin area is between 0.2-2 mm, and
- wherein a width of the foam member is between 3-30 mm, and/or a width-to-thickness ratio of the foam member is between 0.1-30, and/or the foam member is a non-continuous three-dimensional shape.

16. The breathing mask according to claim 15, wherein the foam member has a twisted U-shaped structure in a three-dimensional space.

17. The breathing mask according to claim 15, wherein the foam member has a twisted inverted V-shaped structure in a three-dimensional space.

18. The breathing mask according to claim 15, wherein the foam member has a twisted and spaced inclined symmetrical extension structure in a three-dimensional space.

19. The breathing mask according to claim 15, wherein a cross-section of the foam member is a triangular, quadrilateral, pentagonal, or hexagonal structure; and an edge of the foam member near the user's face has a curved portion.

20. The breathing mask according to claim 15, wherein a permeability of the foam member is less than 50 L/min.

* * * * *